(12) United States Patent
Bauman et al.

(10) Patent No.: US 9,690,903 B2
(45) Date of Patent: Jun. 27, 2017

(54) NON-DICOM OBJECT ATTACHMENT METHOD AND SYSTEM

(75) Inventors: Aaron A. Bauman, Smithville, OH (US); Glenn T. Burke, Cleveland Heights, OH (US); Rem O. Siekmann, Mentor, OH (US)

(73) Assignee: CODONICS, INC., Middleburg Heights ( * ) Notice: Subject to any disclaimer, the term of this patent is extended or adjusted under 35 U.S.C. 154(b) by 1019 days.

(21) Appl. No.: 13/305,737

(22) Filed: Nov. 28, 2011

(65) Prior Publication Data

US 2012/0240067 A1    Sep. 20, 2012

Related U.S. Application Data

(60) Provisional application No. 61/417,450, filed on Nov. 28, 2010.

(51) Int. Cl.
*G06F 3/048* (2013.01)
*G06F 19/00* (2011.01)

(52) U.S. Cl.
CPC ................... *G06F 19/323* (2013.01)

(58) Field of Classification Search
None
See application file for complete search history.

(56) References Cited

U.S. PATENT DOCUMENTS 5,740,267 A *   4/1998   Echerer et al. ............... 382/132
2002/0048222 A1*   4/2002   Wright et al. ................... 369/1

* cited by examiner

*Primary Examiner* — Thanh Vu
(74) *Attorney, Agent, or Firm* — Cooper Legal Group, LLC

(57) ABSTRACT

Provided is a method and apparatus for storing content on a portable computer-readable medium. A computer system receives a request to store a medical image and additional data in a different format on the portable computer-readable medium. The medical image and the additional data to be stored are received in a computer memory, and an association is established between the additional data and the medical image so the additional data is stored with the medical image on the portable computer-readable medium. The medical image and the additional data are stored on the portable computer-readable medium with an application that, when executed by a user computer, grants a user access to both the medical image and the additional data on the portable computer-readable medium.

16 Claims, 12 Drawing Sheets

NON-DICOM OBJECT ATTACHMENT METHOD AND SYSTEM

CROSS-REFERENCE TO RELATED APPLICATIONS

This application claims the benefit of U.S. Provisional Application No. 61/417,450, filed Nov. 28, 2010, which is incorporated in its entirety herein by reference.

BACKGROUND OF THE INVENTION

1. Field of the Invention

This application relates generally to managing electronic data to be stored on a portable computer-readable medium and, more specifically, to a method and system for storing non-DICOM-compliant files and data on a portable computer-readable medium in association with a DICOM study.

2. Description of Related Art

The Digital Imaging and Communications in Medicine ("DICOM") standard was enacted to promote uniformity in the storage and communication of medical images so that such information can be readily shared across platforms of different vendors. To ensure data uniformity the DICOM standard imposes strict requirements on data formatted according to that standard.

Electronic documents formatted as Microsoft® Word and Adobe® PDF documents are not considered to be DICOM compliant. However, physicians, hospitals and other medical caregivers regularly create patient reports and charts, for example, in such non-DICOM formats. These, and other, document formats that are not compliant with have thus far been unable to be stored on the same portable computer-readable medium as a DICOM study for the same patient.

BRIEF SUMMARY OF THE INVENTION

Accordingly, there is a need in the art for system and method for attaching or otherwise associating non-standard-compliant objects and data to/with studies that are compliant with the DICOM or any other medical data standard to be stored on a non-transitory computer-readable medium.

According to one aspect, the subject application involves a method of storing content on a portable computer-readable medium. The method according to the present aspect includes receiving, with a computer system, a request to store, on the portable computer-readable medium, a medical image in a standardized format compliant with a medical imaging standard for communicating medical images between computer systems adapted to receive the medical images in the standardized format. A request to store additional data in a second format, other than the standardized format, on the portable computer-readable medium is also received. The method also includes receiving, in a non-transitory, computer-readable memory operatively connected to the computer system, the medical image and the additional data to be stored on the portable computer-readable medium. The additional data is associated with the medical image so the additional data is stored along with the medical image on the portable computer-readable medium when the medical image is written to the computer-readable medium. The medical image and the additional data are then stored on the portable computer-readable medium with an application, data file, flash file, or any suitable content that, when processed by a user computer, simultaneously or concurrently presents a user with options that are selectable to access both the medical image and the additional data on the portable computer-readable medium.

According to another aspect, the subject application involves a computer system that stores content on a portable computer-readable medium. The computer system includes a request receiving component that receives a request to store, on the portable computer-readable medium, a medical image in a standardized format compliant with a medical imaging standard for communicating medical images between computer systems specially programmed to receive the medical images in the standardized format. The request receiving component also receives a request to store additional data in a second format, different than the standardized format, on the portable computer-readable medium. The second format is a format that is not compliant with a medical imaging standard. The computer system also includes a non-transitory, computer-readable memory that stores the medical image, the additional data to be stored on the portable computer-readable medium, and an application that, when executed by a computer, grants a user access to both the medical image and the additional data on the portable computer-readable medium. A processing component establishes a relationship or otherwise associates the additional data with the medical image so the additional data is stored with the medical image on the portable computer-readable medium. A writing component stores the medical image, the additional data and the application on the portable computer-readable medium as a publication job executed by the computer system.

According to another aspect, the subject application involves a method of presenting content on a portable computer-readable medium provided to a user computer to a user. The method includes with the user computer, determining that the portable computer-readable medium stores a medical image and additional data. The medical image on the portable computer-readable medium is in a standardized format compliant with a medical imaging standard for communicating medical images between computer systems each provided with a viewer specifically adapted to view medical images in the standardized format, and the additional data is in a second format, other than the standardized format, that is not compliant with or otherwise specific to a standard adopted specifically for use in the medical field. Using a display device provided to the user computer, the user is simultaneously, or at least concurrently, presented with options for accessing both the medical image and the additional data in a common user interface. In response to receiving a selection of an option from the user interface to access the medical image input by the user via the user computer, a viewer adapted for displaying the medical image in the standardized format is executed using the user computer to present the medical image to the user. Likewise, in response to receiving a selection of an option from the user interface to access the additional data input by the user via the user computer, a default application installed on the user computer for presenting the additional data in the second format to the user.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
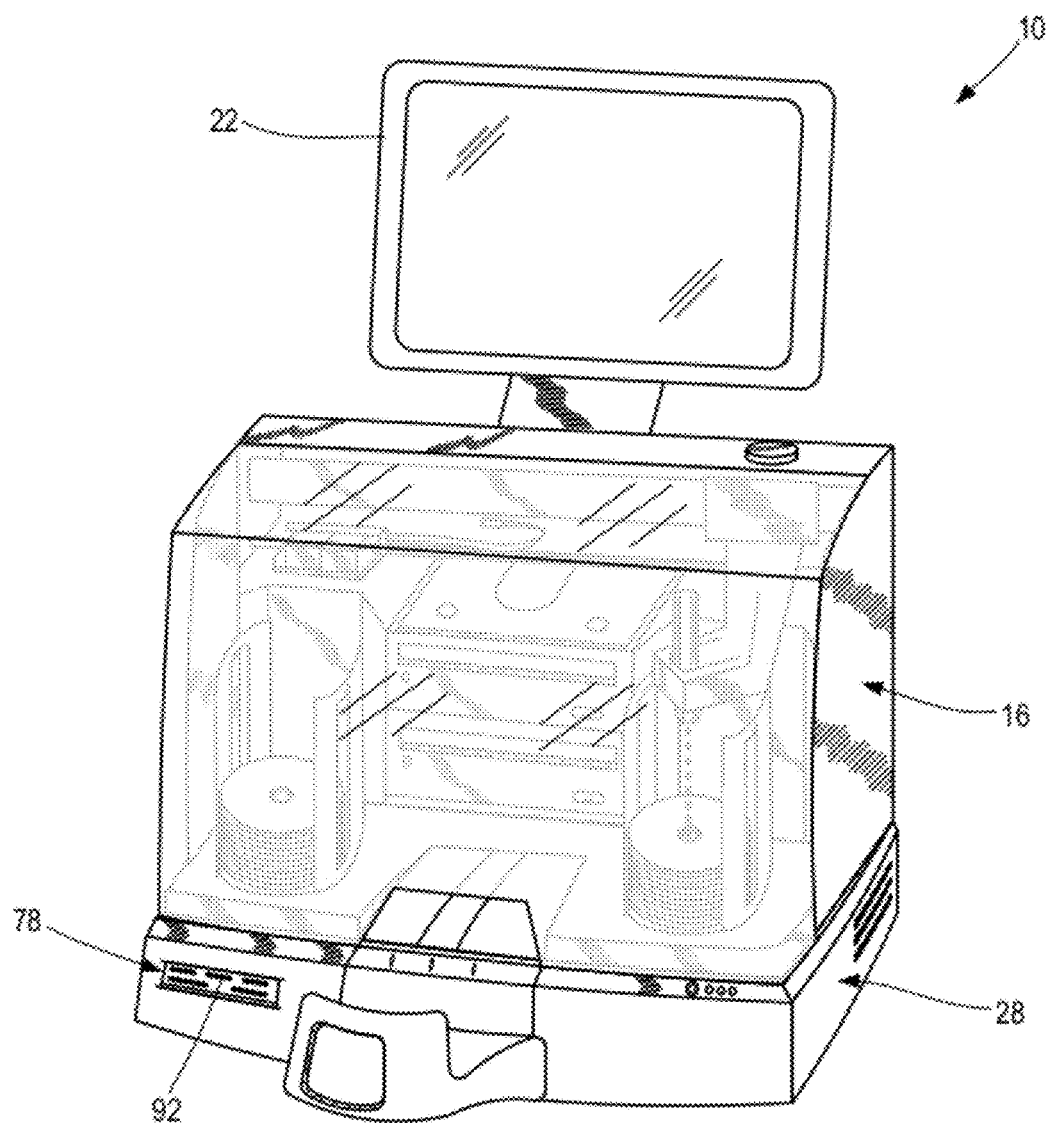
FIG. 1 shows an illustrative embodiment of a publisher for storing a medical image and additional data associated with the medical image onto a portable computer-readable medium.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

Figure 2:
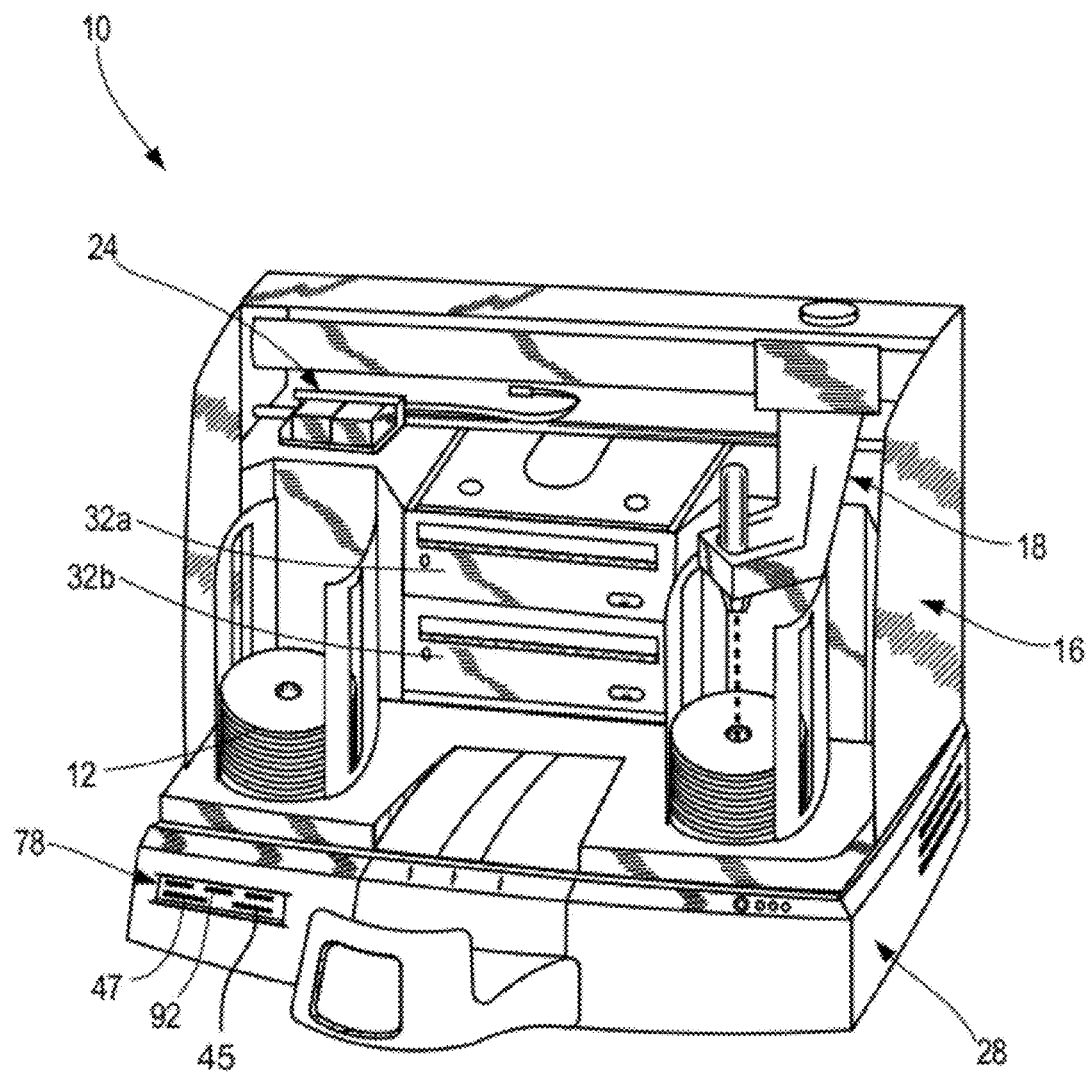
FIG. 2 shows a partially cutaway view of the publisher of FIG. 1.

FIGS. 1 and 2 show an illustrative embodiment of a computer system 10 that stores content on a portable computer-readable medium 12. An example of the computer system 10, interchangeably referred to herein as a publisher 10, is described in U.S. Patent Application Publication No. 2008/0122878 to Keefe et al., the entirety of which is incorporated herein by reference.

Generally, the embodiment of the publisher 10 shown in FIGS. 1 and 2 includes a recorder 16 with one or more optical (e.g., CD, DVD, . . . ) recording bays 32a, 32b (generally referred to as a recording bay 32) for recording the content onto the portable computer-readable medium 12. An automated feeder 18 can be provided to the recorder 16 for transporting the portable computer-readable medium 12 from a storage bin 17 to the recording bay 32 without intervention by an operator once publication of the portable-computer readable medium 12 has been initiated. That is, once an instruction to publish a portable computer-readable medium 12 has been received by the publisher 10, the automated feeder 18 can supply the computer-readable medium 12 retrieved from the storage bin 17 to the appropriate recording bay 32 without further intervention by the operator.

In addition to, or instead of the optical recording bays 32 shown in FIG. 2, the recorder 16 can be provided with an optional recording bay 78 for recording the medical image 94 (FIG. 5) in the standardized format onto a portable computer-readable medium other than an optical medium such as a CD and/or DVD. For example, a USB port 92 (FIG. 1) of the recording bay 78 allows a USB flash drive, external USB hard drive, and the like to be operatively connected to the publisher 10 for storing the medical image 94 thereon, or for optionally delivering the medical image 94, and optionally additional data described below, to be included in the content stored on the computer-readable medium 12. The recording bay 78 can also optionally include additional format ports such as a SD card port 45 and the like, offering yet other alternatives to the optical format portable computer-readable medium 12. The recording bay 78 can optionally also include a smart card port 47 (FIG. 2) in which a so called "smart card" can be received to activate and/or deactivate operational features of the publisher 10. For example, certain options that can be performed by the publisher 10 when activated can be deactivated by insertion of the suitably-programmed smart card, thereby configuring the publisher 10 for an intended end user based on the configuration options purchased by that end user. The active features of the publisher 10 can be changed by replacing and/or reprogramming the smart card. For the sake of brevity, however, the method and apparatus are described below as storing a medical image 94 onto a CD as the computer-readable medium 12.

In addition to the recorder 16 and automated feeder 18, the publisher 10 also includes an display device 22 which, for some embodiments herein can be a touch-screen display panel, for example. The display device 22 is operable to present the operator with one or more options that the operator can select to enter commands to be carried out by the publisher 10 as described in detail below.

Figure 3:
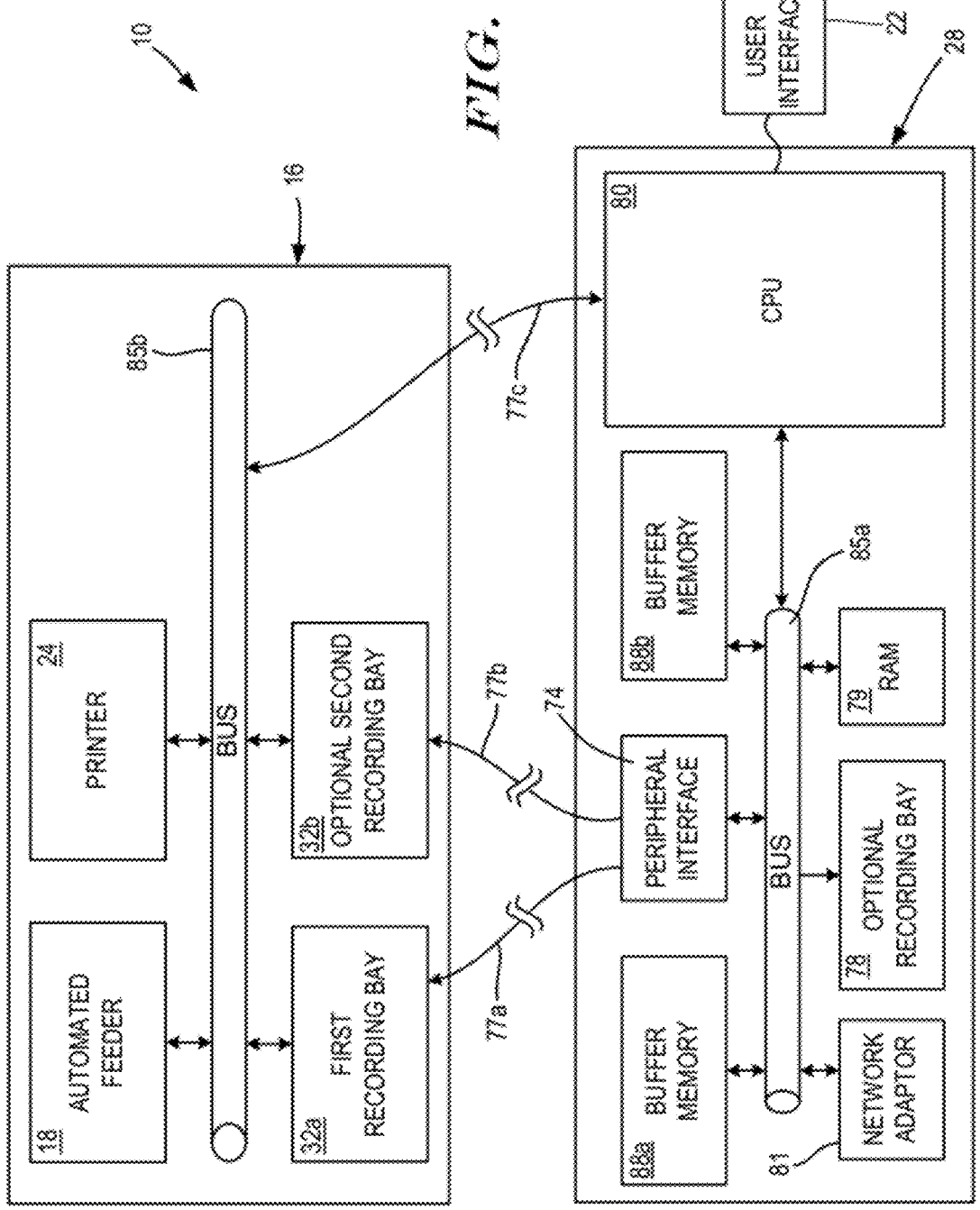
FIG. 3 shows an illustrative embodiment of a block diagram illustrating operational components of a publisher for storing a medical image and additional data associated with the medical image onto a portable computer-readable medium.

A control unit 28 is operatively connected to the recorder 16 to control the storage of content onto the computer-readable medium 12. The embodiment of the control unit 28 appearing in FIG. 3 includes a processing component 80 that executes computer-executable instructions to control operation of the publisher 10 as described herein. A peripheral interface 74 transmits communications over at least one, and optionally a plurality of dedicated data transmission paths 77a, 77b between the control unit 28 and the recorder 16. Each transmission path 77a, 77b is said to be dedicated for transmitting the content to be stored on the computer-readable medium to a respective one of the recording bays 32a, 32b. The content transmitted by the peripheral interface 74 is retrieved from first and second buffer memories 88a, 88b (generally referred to as a buffer memory 88) of the publisher 10 via bus system 85a to be stored on the computer-readable medium 12. The first and second data transmission paths 77a, 77b can be electrically isolated from each other to primarily transmit, or only transmit the content between respective combinations of the first buffer memory and a first recording bay 32a, and the second buffer memory 88b and a second recording bay 32b. Similarly, a dedicated control signal path 77c, separate from the data transmission paths 77a, 77b, can be established between the processing component 80 of the control unit 28 and portions of the recorder 16 controlled by the processing component 80 via a recorder bus system 85b.

Figure 4:
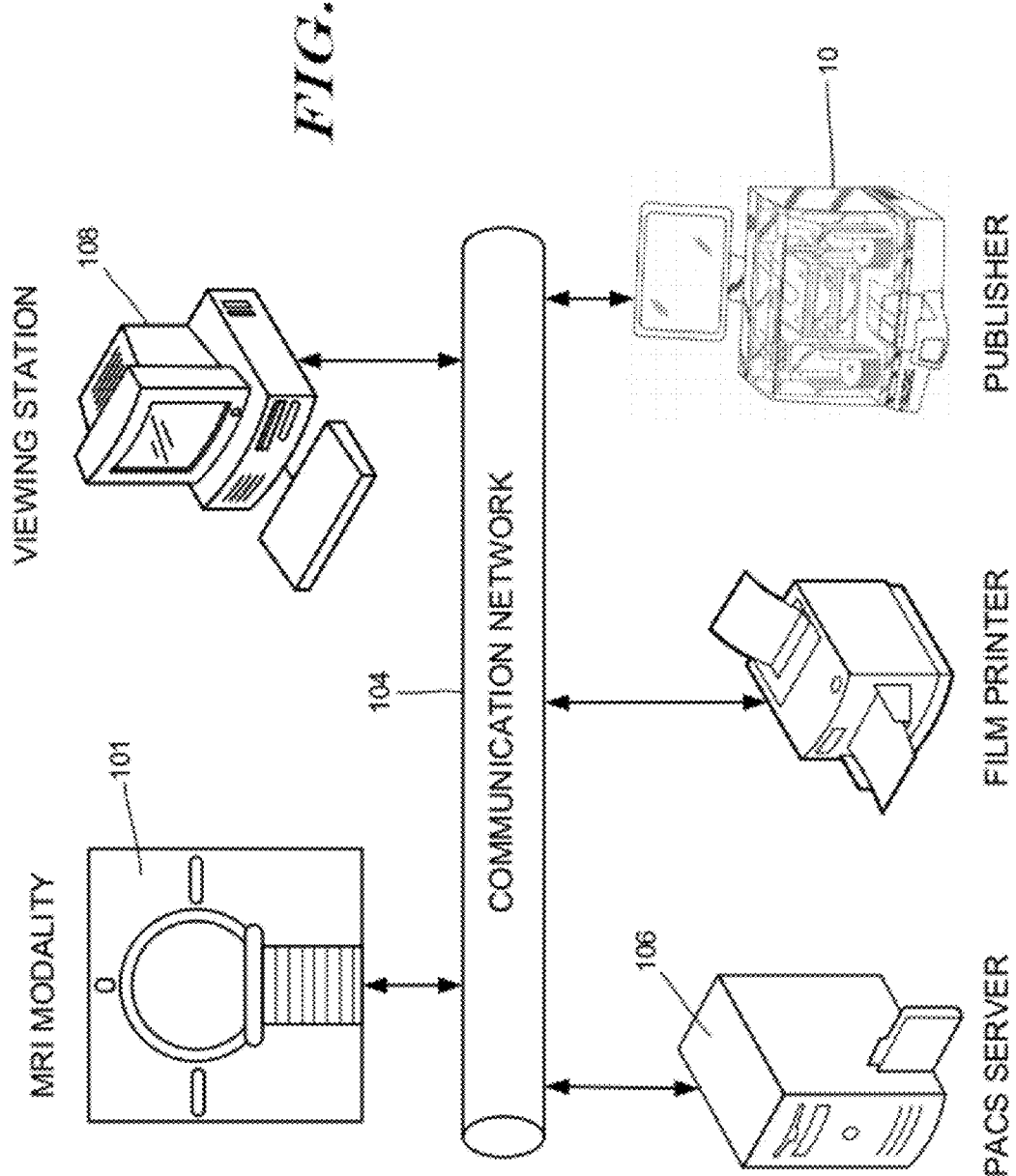
FIG. 4 shows an illustrative embodiment of a communication network that includes a publisher for storing a medical image and additional data associated with the medical image onto a portable computer-readable medium and a plurality of other computer terminals that can act as a source of the medical image and/or additional data.

The control unit 28 also includes computer components such as a volatile operational memory such as random access memory ("RAM") 79 (FIG. 3) for temporarily storing information during operation of the publisher 10. A network adaptor 81, which can be a suitably-programmed wireless network adaptor compliant with the IEEE 802.1x standards, or any high-speed LAN connection such as a 10/100 Ethernet adaptor, for example. The network adaptor 81 enables the publisher 10 to communicate with other compatible terminals via a communication network 104 (FIG. 4). Examples of such communications include receiving the medical image 94, additional data to be stored on the computer-readable medium 12 with the medical image 94, commands issued to the publisher 10, and other communications from a host computer and/or a medical modality 101 (shown as an MRI scanner in FIG. 4). The host computer can optionally be a medical output storage device such as a PACS server 106, a computer workstation 108 programmed with compatible viewing software for opening and presenting medical images such as those stored in compliance with the DICOM standard, or any other computer storage device in communication with the network 104.

The network adaptor 81, and publisher 10 in general, can communicate with the host computer via any conventional network communication protocol such as TCP/IP, for example, and/or can optionally be hardwired directly to the publisher 10 via a USB, Ethernet, Firewire, or any other suitable connector. The host computer can optionally be remotely located relative to the publisher 10, separated from the publisher 10 via the communication network 104. Being remotely located, the host computer can optionally also be located in a separate room or physical location relative to the publisher 10.

The computer-readable medium 12 on which the content is to be stored is said to be portable in that it is a mass storage medium that can be hand carried, delivered by a courier or otherwise physically transported between the publisher 10 and a user's computer. Thus, the computer-readable medium 12 is physically transportable by hand, without requiring electricity to maintain storage of the content thereon while in transit, between the publisher 10 and the user's computer. The portable computer-readable medium 12 can be a passive medium to be temporarily inserted into a compatible drive unit of a personal computer or other computer terminal for retrieving and reviewing the content there from. Examples of suitable portable computer-readable media 12 include, but are not limited to, optical media such as a compact disc (also commonly referred to as a "CD", "CD-ROM", "CD+R", "CD-R", "CD-RW"—collectively referred to herein as "CD"); digital video disc (also commonly referred to as a "digital versatile disc," and including "DVD", "DVD-ROM", "DVD-R", "DVD-RW", "DVD+R", "DVD+RW", "DVD-RAM", and the like—collectively referred to herein as "DVD"); Blu-ray Discs such as BD-R, BD-RE, and the like—collectively referred to herein as "Blu-ray Disc"); HD-DVD; and the like. Another suitable portable computer-readable medium 12 includes a USB flash drive commonly referred to as a jump drive or memory key that includes an EEPROM based memory integrated with a USB interface.

Although described herein as being a stand-alone unit comprising an automated feeder and integrated display 22, the publisher 10 can be implemented using any computerized terminal comprising a recording bay, non-transitory memory, and processor, such as a general purpose computer, for example.

Figure 5:
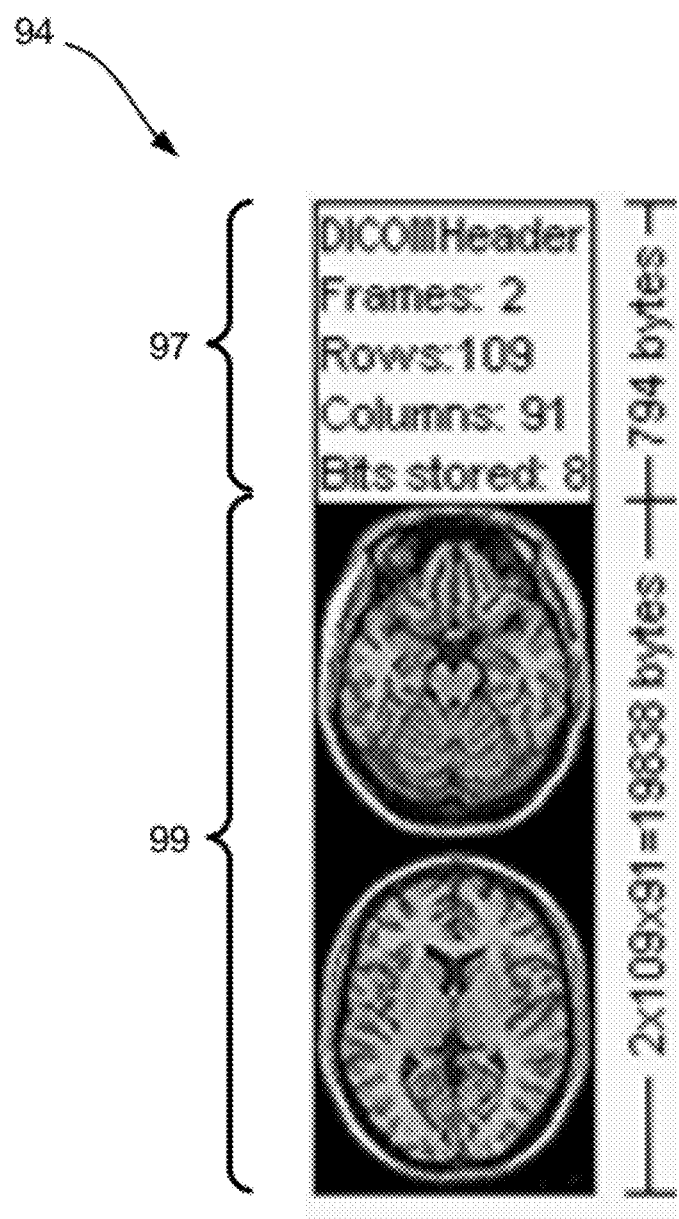
FIG. 5 shows an illustrative embodiment of a medical image in a standardized format compliant with a medical imaging standard for communicating medical images between computer systems adapted to receive the medical images in the standardized format.

FIG. 5 shows an illustrative embodiment of a medical image in a standardized format compliant with a medical imaging standard for communicating medical images between computer systems adapted to receive the medical images in the standardized format. As shown, the medical image 94 is a magnetic resonance image ("MRI") file formatted in compliance with the DICOM standard, which is a format dedicated for medical images and other medical data to promote communications between otherwise independent parties. In this example, a DICOM header 97 is integrated as an inseparable part of the medical image 94, and includes 794 bytes of information pertaining to image data 99 included in the medical image 94. The image data 99 can be interpreted by a computer executing a DICOM-compatible viewer to reproduce the medical image 94 to be observed by an end user.

According to other embodiments, the information within the DICOM header 97 can vary depending on the type of the image within the medical image file 94. A representative list of information and parameters to be defined in the DICOM header 97 is included in Part 3 (PS 3.3-2008) of the DICOM standard for various image types, such information to be included in the DICOM header 97 being incorporated in its entirety herein by reference. Examples of information commonly found in the DICOM header 97 include, but are not limited to: the modality used to capture the image appearing in the medical image file 94; the image dimensions; the file size; the Transfer Syntax Unique Identification ("UID") indicating whether, and optionally a type of compression used on the image data 99; the byte order of the image data 99; MRI echo time, the samples per pixel, photometric interpretation, and bits allocated. To minimize the likelihood of the DICOM header 97 getting separated from the image data 99 both the DICOM header 97 and the image data are integrally combined to form the medical image file 94 that is compliant with the DICOM standard.

The DICOM standard supports images captured by a variety of different medical modalities, including, but not limited to:

BI=Biomagnetic Imaging
CR=Computed Radiography
CT=Computed Tomography
DG=Diaphanography
DM=Digital Microscopy
DX=Digital X-Ray
ES=Endoscopy
HC=Hard Copy
LS=Laser Surface Scan
MG=Mammography
MR=Magnetic Resonance
NM=Nuclear Medicine
OT=Other
PT=Positron Emission Tomography (PET)
RF=Radio Fluoroscopy
RG=Radiographic Imaging (conventional film screen)
RTDOSE (a.k.a. RD)=Radiotherapy Dose
RTIMAGE=Radiotherapy Image
RTPLAN (a.k.a. RP)=Radiotherapy Plan
RTSTRUCT (a.k.a. RS)=Radiotherapy Structure Set
SR=Structured Reporting
TG=Thermography
US=Ultrasound
XA=X-Ray Angiography
XC=eXternal Camera
ECG=Electrocardiograms In use, a request to store a medical image on the computer-readable medium 12 is received by a receiving component of the publisher 10. The medical image 94 to be stored is in a standardized format, such as the DICOM format for example, that is compliant with a medical imaging standard for communicating medical images between computer systems operated by unrelated parties. The receiving component can include at least one of the network adaptor 81, the display device 22, a keyboard and/or mouse (not shown) or any other input hardware that can be used to receive such a request input by an operator to the publisher 10 to store the medical image 94 on a computer-readable medium 12. The receiving component can optionally also include computer-executable instructions that, when executed by the processor component 80, enable the publisher 10 to process the request as part of the method described herein.

Figure 6:
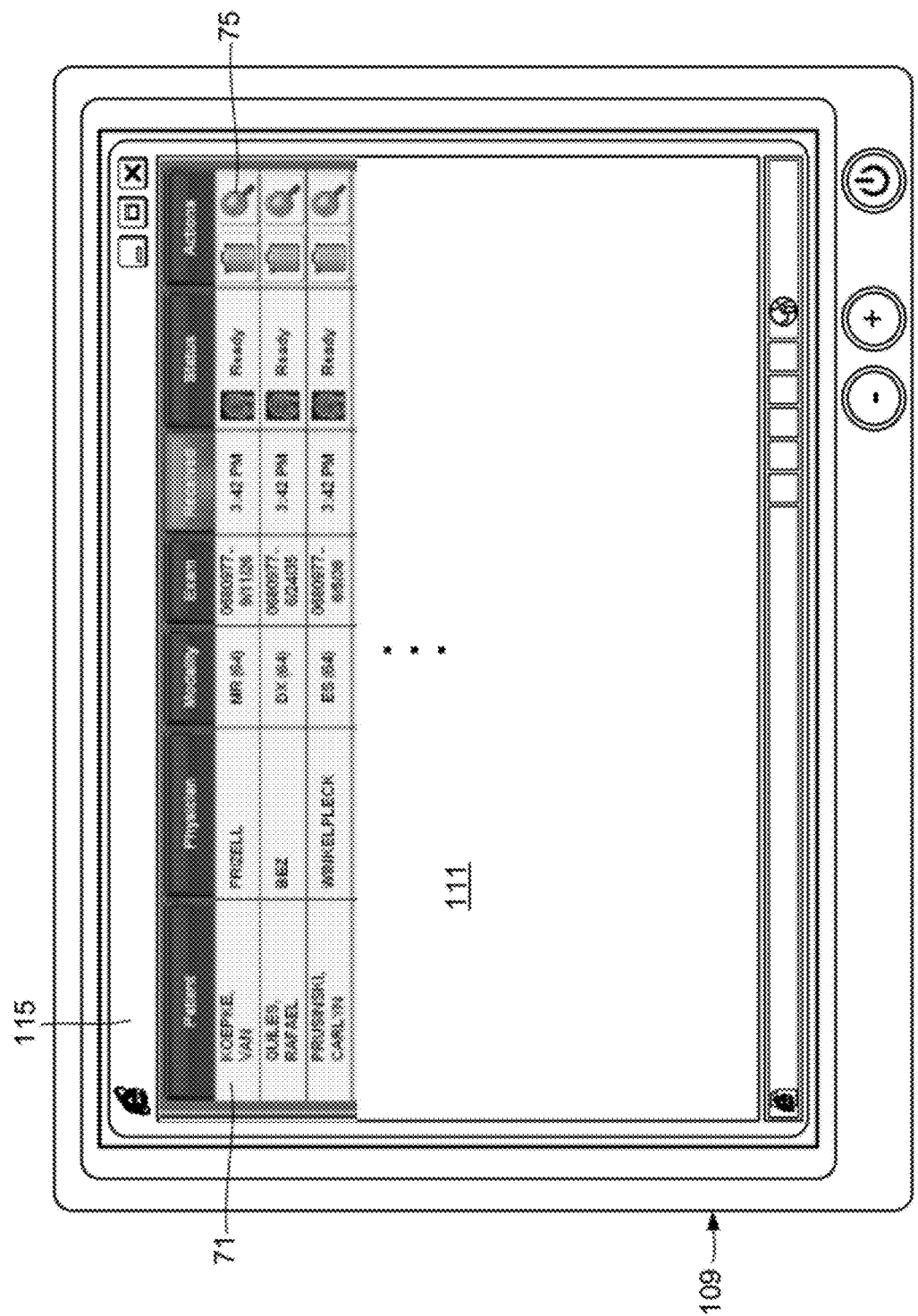
FIG. 6 shows an illustrative embodiment of an operator interface displaying jobs to be performed by a publisher to store content on a computer-readable medium.

FIG. 6 shows an embodiment of a display device, such as a monitor 109 provided to the computer workstation 108 (FIG. 4) showing an operator interface 111 displaying a plurality of requests for the publisher 10 to store content on the computer-readable medium 12. The requests can be received by the publisher 10 or other network-accessible device, and assembled into jobs, each of which constitute a separate recording process to be performed by the publisher 10 to store content onto a computer-readable medium 12. For example, a first request is included in a job 71 arranged in a queue of recording jobs to be performed by the publisher 10 presented as part of the operator interface 111. The job 71 includes at least one medical image 94 pertaining to a patient by the name "Van Koepke" to be stored on a CD, for example. Upon being added to the job 71, the medical image 94 is transmitted from its storage location to the publisher 10 to be stored in the buffer memory 88, from where it will be stored onto the computer-readable medium 12 when the job 71 is executed by the publisher 10.

The operator interface 111 can be displayed by a so-called web-browser application 115, which displays network resources retrieved according to the Hypertext Transfer Protocol (HTTP), or other protocols, in a manner analogous to a website by the workstation 108. As such, the data for generating the operator interface 111 can be stored on the publisher 10 or other network-accessible storage location and served over the communication network 104 when the operator enters the corresponding uniform resource locator or other information indicative of the network address of the operator interface into the web-browser application 115.

The receiving component of the publisher 10 can also receive a request to store additional data in a second format, other than the standardized format, on the portable computer-readable medium 12. For example, physicians can prepare documents such as reports formatted as Microsoft Word documents, pdf documents, or any other format that is not specific to the field of medicine or the provision of health care to patients. The DICOM standard, for example, does not consider such document formats, and does not therefore accommodate the use of such document formats in combination with medical images that are formatted to be DICOM compliant.

Figure 7:
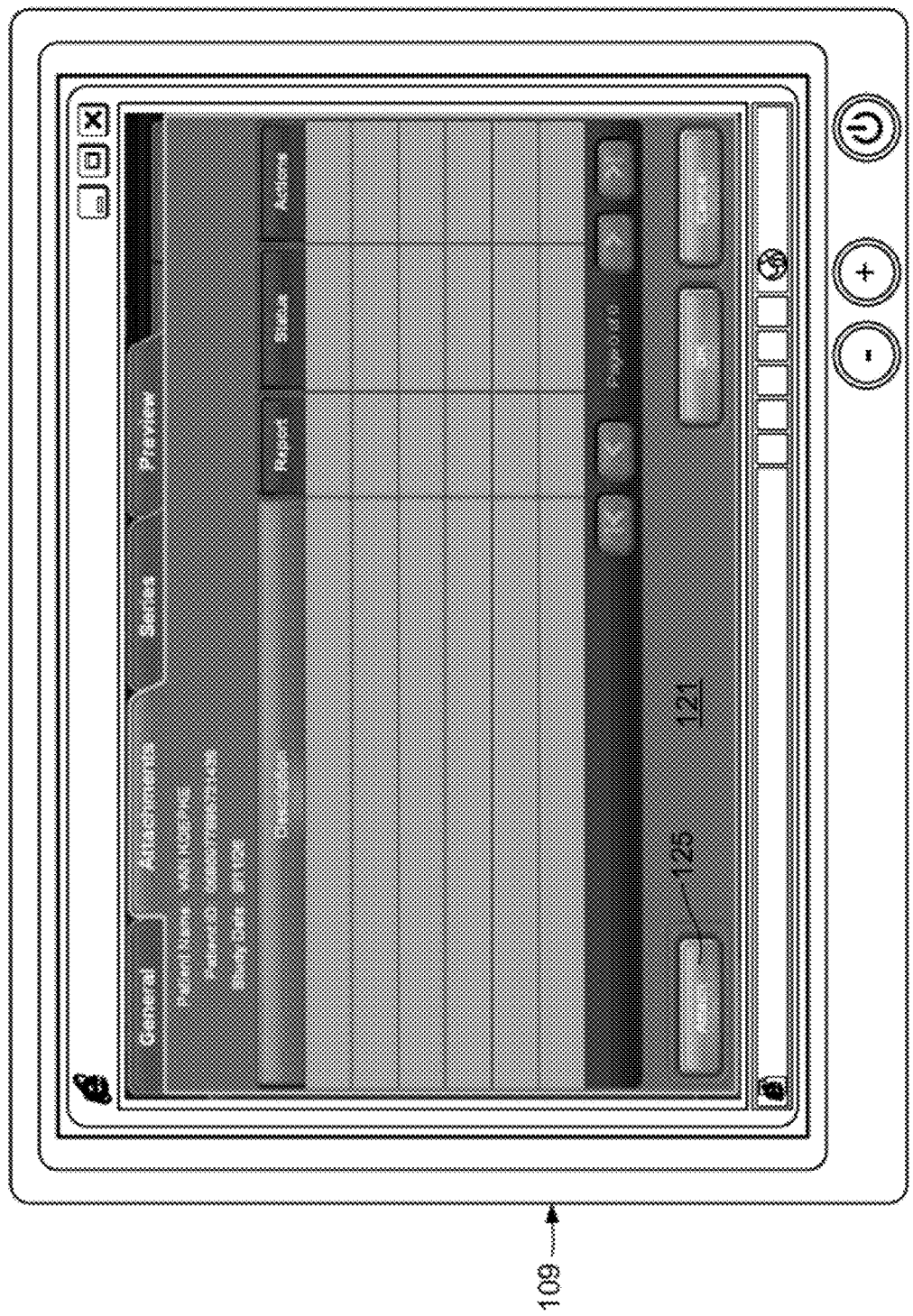
FIG. 7 shows an illustrative embodiment of an attachment screen where additional data can be selected to be associated with a medical image.

To submit a request to store the additional data with the DICOM-compliant medical image 94 on the same computer-readable medium 12, an operator can access the operator interface 111 illustrated in FIG. 6 and select an action icon 75 appearing as part of the operator interface 111. In response to selecting the action icon 75, an attachment screen 121 such as that shown in FIG. 7 can be presented in the web-browser application displayed by the monitor 109. The attachment screen 121 includes an "Attach" soft key 125 that is selectable by the operator to select the additional data in the non-standardized format to be stored on the computer-readable medium 12 along with the medical image 94 in the standardized format.

Figure 8:
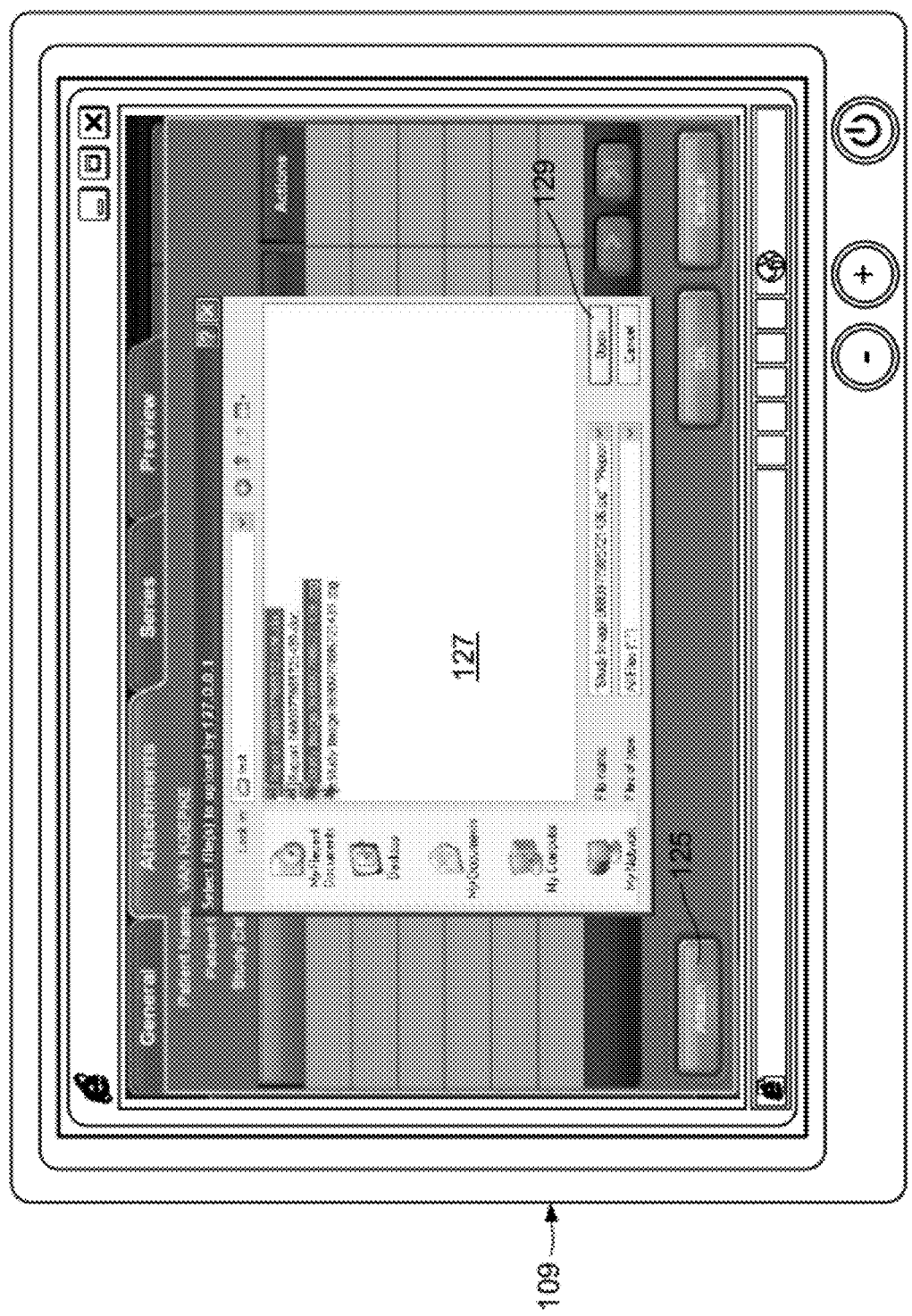
FIG. 8 shows an illustrative embodiment of a dialog box for selecting individual files to be associated as additional data with a medical image to be stored on a computer readable medium.

Selection of the Attach soft key 125 opens a dialog box 127, shown in FIG. 8, presenting the operator with a menu for selection of the additional data to be stored with the medical image 94 on the computer-readable medium 12. The additional data can include one or a plurality of individual documents or files stored locally on a hard disk drive provided to the computer workstation 108, stored on a file server or other storage device accessible over the communication network 104, or any other data from a source that is locally accessible to the workstation 108 or network accessible via the workstation 108 to be transmitted over the communication network 104 to the publisher 10. Regardless of the storage location of the additional data, the workstation 108 and/or the operator can optionally be required to have a required level of permission to access the additional data at its storage location to transmit that additional data to the publisher 10.

According to alternate embodiments, the display device 22 provided to the publisher 10 can optionally display the operator interface 111, the attachment screen 121 and dialog box 127 to select additional data locally stored on a memory device such as the buffer memory 88, for example. However, for receiving the additional data from other storage locations externally of the publisher, the publisher 10 can optionally be restricted to only receive the additional data when transmitted from those other storage locations. In other words, to receive the additional data from other, external storage locations, the additional data is required to be transmitted either the workstation 108 from where the request is being submitted, or transmitted from a network storage location that the workstation 108 is permitted to access. Initiating transmission of the additional data to the publisher 10 from an external storage location can optionally be prevented using the publisher 10 itself to initiate the request. Thus, according to such embodiments, the additional data is to be "pushed" to the publisher 10, but can not be "pulled" by the operator using the publisher 10 to submit a request.

Figure 9:
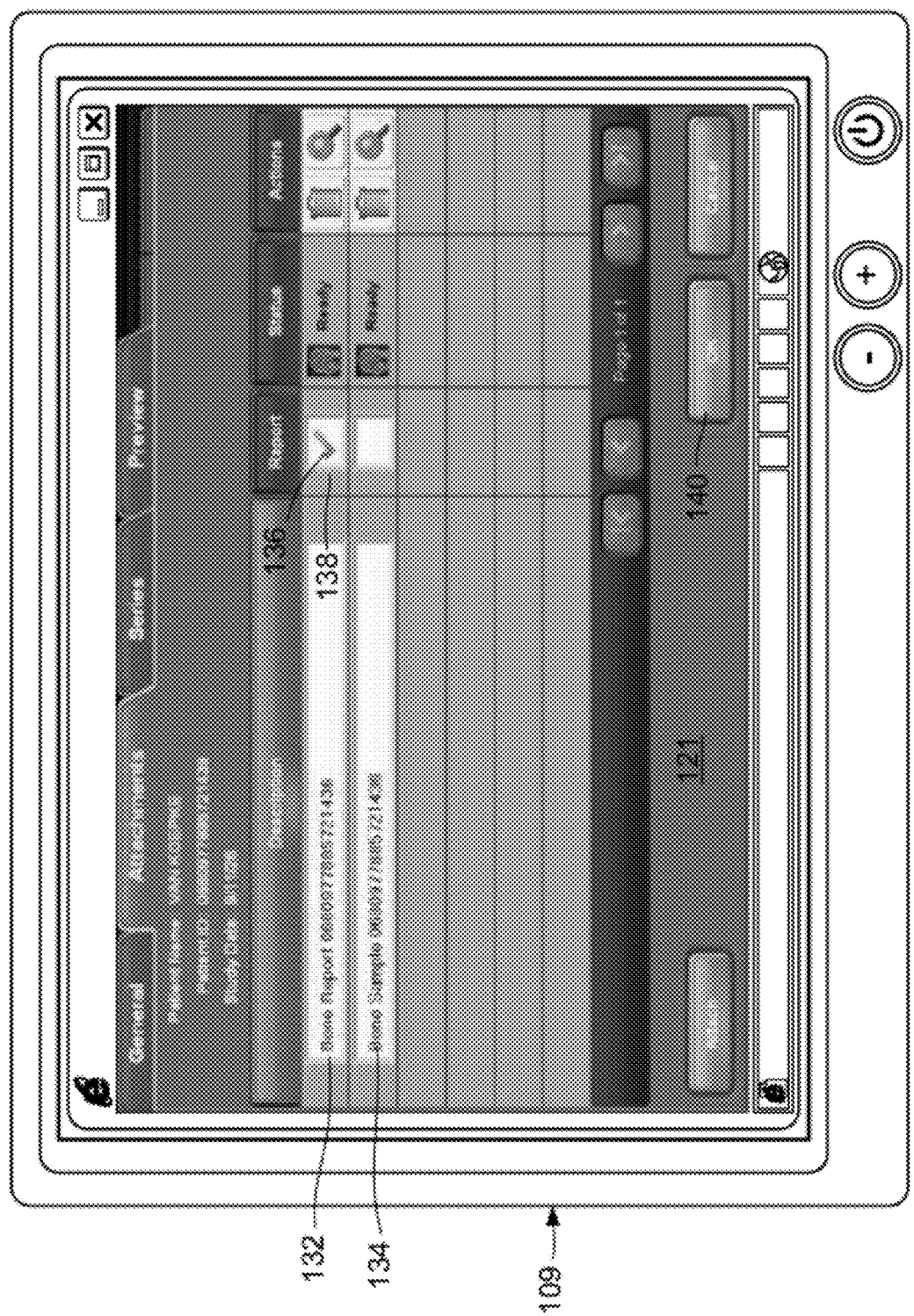
FIG. 9 shows an illustrative embodiment of the attachment screen of FIG. 7, including a plurality of entries to be associated with the medical image, including one entry that has been categorized.
Figure 10:
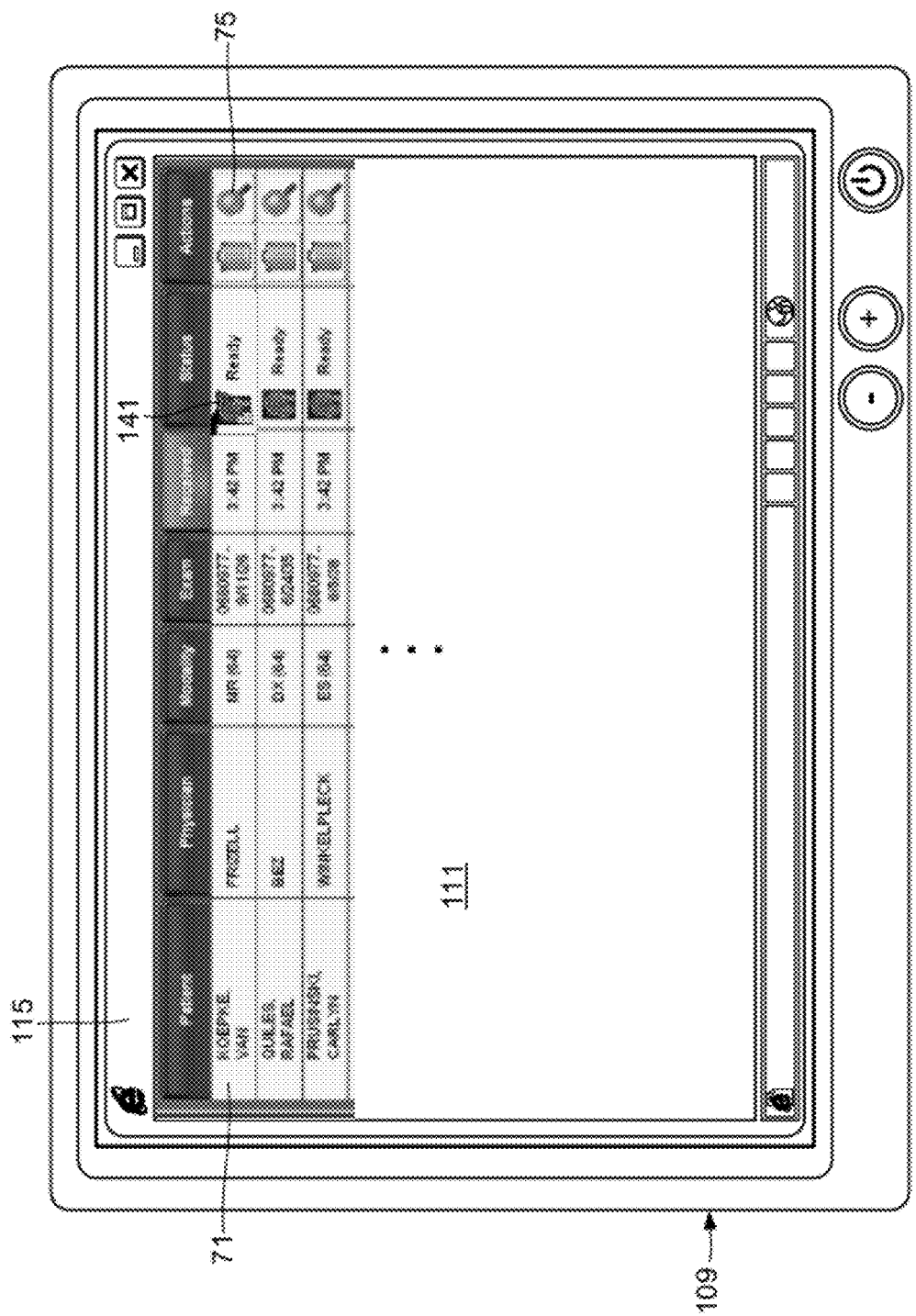
FIG. 10 shows an illustrative embodiment of the operator interface including a marker distinguishing a job including associated additional data from jobs without associated additional data.

Once the additional data to be stored on the computer-readable medium 12 is selected in the dialog box 127, the open button 129 can be actuated to include each separate additional data selected as a separate attachment entry 132, 134 in the attachment screen 121, as shown in FIG. 9. As shown, each attachment can optionally be categorized as a predetermined type of additional data. For example, physicians typically prepare reports summarizing the findings of an examination. The operator selecting the additional data can manually input an indication that the additional data entry falls within that predetermined category of data. In the example shown in FIG. 9, entry 132 includes a report, so the operator has manually inserted a check 136 into the report checkbox 138, designating that entry 132 as a report. According to alternate embodiments, the word "report" can optionally be automatically recognized by the workstation 108 running the attachment screen 121 in the description of the entry 132, and the check 136 automatically inserted into the report checkbox 138. Each entry of additional data designated as falling in a predetermined category can be categorized and stored in a folder specifically designated for that category created by the publisher 10 when storing the content on the computer-readable medium 12. Thus, when a plurality of different types of additional data are presented to the end user, the additional data can be presented in separate categories.

Each entry of additional data is transmitted to the publisher 10 to be stored in the buffer memory 88 of the publisher 10, from where it is to be stored onto the computer-readable medium 12 as part of the job during which the medical image 94 is also to be stored thereon. Once each desired entry of additional data has been selected to be uploaded to the publisher 10, the process of requesting additional data to be stored on the computer-readable medium can be concluded by selection of the "OK" button 140. The operator is returned to the operator interface 111 in response to selection of the OK button 140. However, the job 71 including the medical image 94 and now the associated additional data for patient "Van Koepke" now includes a marker 141 indicating that the job 71 includes additional data associated with the medical image 94 to be stored on the computer-readable medium 12. In other words, the publisher 10 has established a relationship between the medical image 94 and the additional data or otherwise associated the additional data with the medical image 94 so the additional data is stored on the computer-readable medium in addition to the medical image 94 when the job 71 is executed by the publisher 10.

As mentioned above, the medical image 94 is formatted in compliance with the DICOM or other medical specific standard. As such, the viewer that is operable to reproduce the medical image 94 in that format is not typically available on an end user's computer. For instance, patients who wish to view their medical image 94 at home may lack the viewer application enabling them to do so. Accordingly, the job 71 can optionally be configured to store a compatible viewer application for reproducing the medical image 94 on the computer-readable medium. Thus, the end user can elect to open the medical image 94, thereby causing the compatible viewer to be executed from the computer-readable medium and enabling the end user to observe the medical image 94. According to alternate embodiments, the job 71 can optionally include an identification of a compatible viewer suitable to open the medical image 94. For instance, a file extension specific to the medical imaging standard can identify a compatible viewer. The compatible viewer can optionally be locally stored on the user computer and launched from a computer memory such as a hard drive of the user computer in response to a user's selection of the medical image from the computer-readable medium 12. The viewer according to other embodiments can be network accessible over the Internet, for example. For such an embodiment, a network address or other location of the compatible viewer can be included on the computer-readable medium 12, allowing the user computer to access the compatible viewer to present the medical image 94 to the user. Thus, the viewer can optionally be stored on the computer-readable medium 12 by the computer system 10 to be executed from the computer-readable medium 12; the viewer can optionally be identified on the computer-readable medium 12 by the computer system 10; the viewer can optionally be locally stored by the user computer and executed from the user computer, or any combination thereof.

Figure 11:
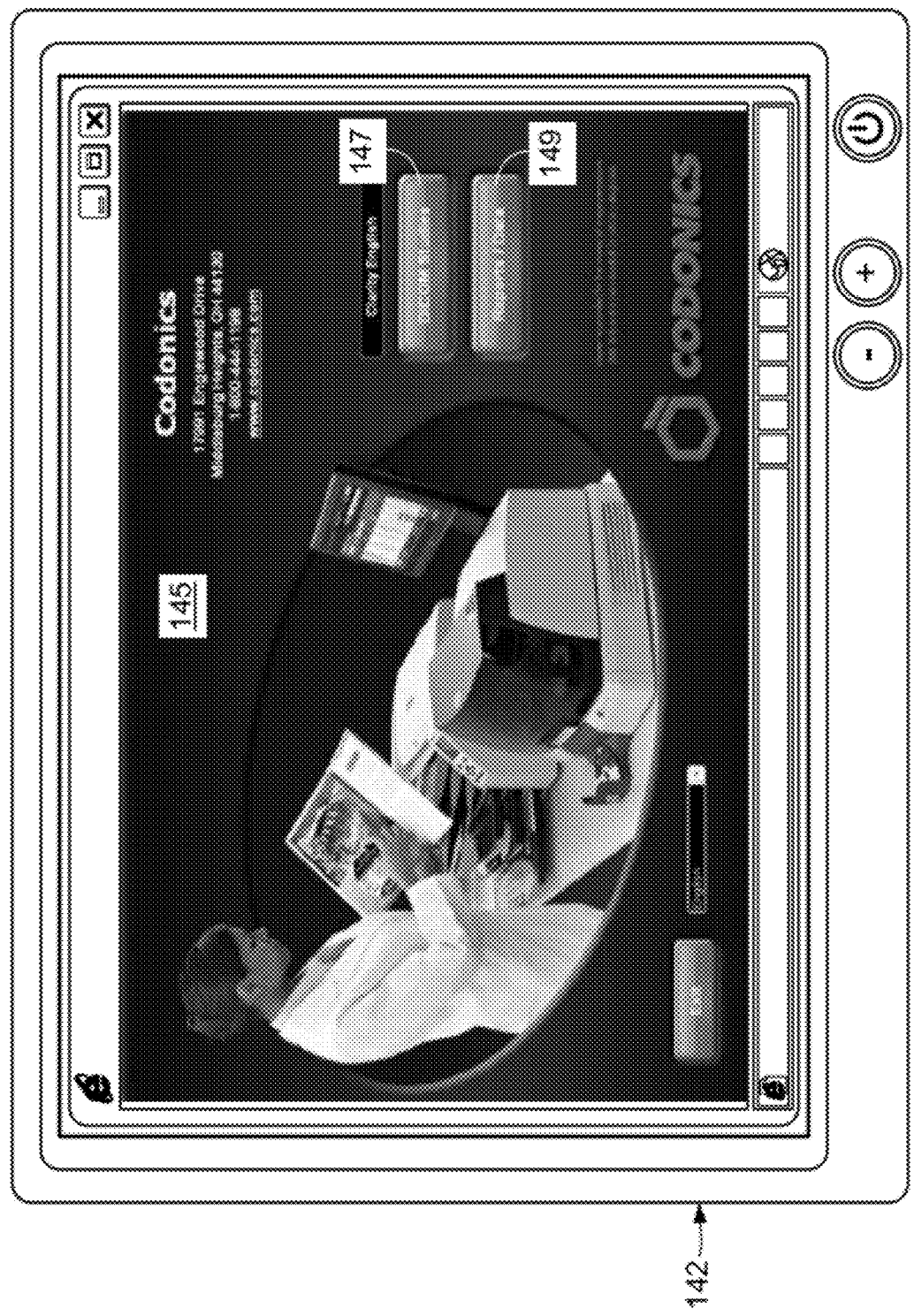
FIG. 11 shows an illustrative embodiment of a display device provided to a user computer displaying an end user interface comprising both an option to access a standardized medical image and an option to access additional data associated with the standardized medical image in a common display.

FIG. 11 shows an illustrative embodiment of a display device 142 provided to a user computer to which the computer-readable medium storing the medical image, additional data and viewer has been introduced. The user computer can be a general purpose computer owned by the patient, and the computer system 10 can optionally be operated by a hospital or other health care facility, for example. When the computer-readable medium 12 storing the medical image 94 and additional data is introduced to the user computer, an auto-run feature can present the splash screen 145 of an application executed from the computer-readable medium on the display device 142 shown in FIG. 11. The application for presenting the splash screen 145 can also optionally be stored on the computer-readable medium 12 during executing of the job performed to store the medical image and the additional data on the computer-readable medium 12, optionally along with the viewer as well. According to alternate embodiments, instead of or in addition to an executable application, the computer-readable medium 12 can optionally store a data file, java file, flash file, or any suitable content that can be opened or otherwise processed using an application installed on the user computer and/or on the computer-readable medium 12 to generate the splash screen 145. The splash screen 145 shown in the embodiment appearing in FIG. 11 simultaneously, or at least concurrently, presents the end user with both an option 147 to access the standardized medical image 94 in the DICOM format, and an option 149 to access the additional data not included in a DICOM study that was associated with the medial image 94, but is in a different, non-medical-specific format. Other embodiments of the splash screen 145, however, can display hyperlinks, icons or any other identifiers in a common user interface that presents the user the option to access the medical image and the additional data stored on the computer-readable medium 12. Thus, the end user can be presented with both options 147, 149 in a common user interface, facilitating ready access to both DICOM study data such as the medical image 94 and the additional data.

Figure 12:
FIG. 12 shows an illustrative embodiment of a menu presented to a user for selecting additional data to be opened.

Selection of the option 149 to access the additional data causes the end user's computer to evaluate the computer-readable medium 12 to locate the additional data thereon, and opens the menu 151 presenting the additional data for selection by the end user as shown in FIG. 12. As shown, the additional data is arranged on the computer-readable medium in folders, under the top-level folder 155 with the patient's name. The first sub-folder 157 designates the subject of the additional data (e.g., heart information) and the date on which the additional data was created/captured. The reports, which were categorized as described above, are arranged in a folder 159 bearing the name of that category, and a generalized folder 161 contains the remainder of the uncategorized additional data on the computer-readable medium 12. From the menu 151 the end user can highlight the additional date desired to be reviewed, and select the open button 165 to execute a local application on the end user's computer compatible for reproducing the opened additional data. Based on the format of the additional data selected to be opened, a default application installed locally on the user computer can be executed to present the additional data to the user via the display device 142. For example, if it is determined that the additional data selected is a Microsoft® Word™ document based on the extension ".doc" appearing at the end of the file name, Microsoft® Word™ can be automatically launched to present the user with the selected document in response to the user computer's receipt of the instruction to open that document. If, however, the default application can not be determined and/or is not locally installed on the user computer, the user computer can optionally display a dialog box requesting the user to specify the default application to be used to open the additional data.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of storing content on a portable computer-readable medium, the method comprising:
    with a computer system, receiving a request to initiate transmission, from an image archive, of a medical image in a standardized format compliant with a medical imaging standard for communicating medical images between computer systems adapted to receive the medical images in the standardized format to be stored onto the portable computer-readable medium as part of a publishing operation;
    receiving a request to initiate transmission of additional data in a second format, other than the standardized format, from a computer memory device to be stored on the portable computer-readable medium with the medical image during the publishing operation, wherein the additional data in the second format is not usable in combination with the medical image in the standardized format;
    receiving, in a non-transitory, computer-readable memory operatively connected to the computer system, the medical image and the additional data to be stored on the portable computer-readable medium during the publishing operation;
    associating the additional data with the medical image so the additional data is stored with the medical image on the portable computer-readable medium during the publishing operation; and
    initiating the publishing operation comprising storing the medical image and the additional data on the portable computer-readable medium with a file management application that, when executed by a user computer to which the portable computer-readable medium has been introduced, provides a user with a common user interface including a menu of selectable options that are manually selectable by the user to access both the medical image on the portable computer-readable medium and the additional data on the portable computer-readable medium from the common user interface.

2. The method of claim 1, wherein the medical image in the standardized format requires a viewer compliant with the standardized format adapted to present the medical image in the standardized format to the user, and cannot be presented by another application used to present the additional data to the user.

3. The method of claim 2 further comprising storing the viewer on the portable computer-readable medium with the medical image and the additional data during the publishing operation.

4. The method of claim 3, wherein the viewer is automatically executed in response to the user accessing the medical image with the application.

5. The method of claim 4, wherein the viewer is executable from the portable computer-readable medium.

6. The method of claim 1, wherein said receiving the additional data comprises receiving a file over a communication network, wherein the file is stored in a memory provided to a remotely-located computer terminal that transmitted the request to store the additional data on the portable computer-readable medium.

7. The method of claim 1, wherein the medical imaging standard is a DICOM standard.

8. A computer system that stores content on a portable computer-readable medium, the computer system comprising:
    a request receiving component that receives:
        a request to initiate transmission, from an image archive, of a medical image in a standardized format compliant with a medical imaging standard for communicating medical images between computer systems adapted to receive the medical images in the standardized format to be stored on the portable computer-readable medium as part of a publishing operation, and
        a request to initiate transmission of additional data in a second format, other than the standardized format, from a computer memory device to be stored on the portable computer-readable medium with the medical image during the publishing operation, wherein the additional data in the second format is not usable in combination with the medical image in the standardized format;
    a non-transitory, computer-readable memory that stores the medical image, the additional data to be stored on the portable computer-readable medium, and a file management application that, when processed by a user computer, provides a user with a common user interface including a menu of selectable options that are manually selectable by the user to access both the medical image on the portable computer-readable medium and the additional data on the portable computer-readable medium from the common user interface;
    a processing component that associates the additional data with the medical image so the additional data is stored with the medical image on the portable computer-readable medium during the publishing operation; and a writing component that initiates the publishing operation and stores the medical image, the additional data and the file management application on the portable computer-readable medium.

9. The computer system of claim 8, wherein the request receiving component comprises a network interface that receives the request to transmit and store the medical image and the request to transmit and store the additional data as a network communication over a communication network.

10. The computer system of claim 8, wherein the additional data is locally stored in a computer memory provided to a remotely-located computer terminal from where the request to transmit and store the additional data is transmitted.

11. The computer system of claim 8 further comprising a user interface that an operator uses to enter the request to transmit and store the medical image on the portable computer-readable medium.

12. A method of presenting content on a portable computer-readable medium provided to a user with a user computer, the method comprising:
   with the user computer, determining that the portable computer-readable medium stores a medical image and additional data, wherein the medical image is in a standardized format compliant with a medical imaging standard for communicating medical images between computer systems each provided with a viewer specifically adapted to view medical images in the standardized format, and the additional data is in a second format, other than the standardized format;
   on a display of the user computer, presenting the user with a common user interface of a file management application stored on the portable computer-readable medium including a menu of selectable options that are manually selectable by the user for accessing both the medical image and the additional data on the portable computer-readable medium to be opened from the portable computer-readable medium;
   in response to receiving a selection of a first selectable option manually selected by the user from the common user interface to access the medical image input by the user via the user computer, executing the viewer from the portable computer-readable medium using the user computer to present the medical image to the user; and
   in response to receiving a selection of a second selectable option from the common user interface to access the additional data input by the user via the user computer, executing a default application installed on the user computer for opening and displaying the additional data from the portable computer-readable medium in the second format to the user.

13. The method of claim 12, wherein the medical image format is medical imaging standard is a DICOM-compliant format.

14. The method of claim 12, wherein the default application is executable from a computer memory provided to the user computer.

15. The method of claim 12, wherein said presenting the user with the common user interface is initiated automatically, as an autorun feature, in response to introduction of the portable computer-readable medium to the user computer.

16. The method of claim 12, wherein said presenting the additional data in the second format to the user comprises:
   determining that the additional data comprises a plurality of different data types; and
   categorizing the plurality of different data types by type when displayed to the user via the user computer.

* * * * *